(12) United States Patent
Van Den Boogaard et al.

(10) Patent No.: US 11,726,737 B2
(45) Date of Patent: Aug. 15, 2023

(54) APPARATUS, METHOD, AND COMPUTER PROGRAM FOR IDENTIFYING A USER OF A DISPLAY UNIT

(71) Applicant: KONINKLIJKE PHILIPS N.V., Eindhoven (NL)

(72) Inventors: Maarten Van Den Boogaard, Heerenveen (NL); Robert Godlieb, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/277,969

(22) PCT Filed: Oct. 8, 2019

(86) PCT No.: PCT/EP2019/077206
§ 371 (c)(1),
(2) Date: Mar. 19, 2021

(87) PCT Pub. No.: WO2020/074503
PCT Pub. Date: Apr. 16, 2020

(65) Prior Publication Data
US 2021/0382673 A1  Dec. 9, 2021

(30) Foreign Application Priority Data
Oct. 10, 2018 (EP) .................... 18199615

(51) Int. Cl.
*G06F 3/147* (2006.01)
*A47G 1/02* (2006.01)
(Continued)

(52) U.S. Cl.
CPC ............... *G06F 3/147* (2013.01); *A47G 1/02* (2013.01); *G02B 5/08* (2013.01); *G06F 3/017* (2013.01); *G06F 21/34* (2013.01)

(58) Field of Classification Search
CPC .......... G06F 3/147; G06F 3/017; G06F 21/34; A47G 1/02; G02B 5/08; G16H 10/00
See application file for complete search history.

(56) References Cited

U.S. PATENT DOCUMENTS

2013/0145272 A1\* 6/2013 Boggie ................... G06F 3/167
                                                              715/728
2017/0199576 A1   7/2017 Schmitz-Le
2018/0004926 A1\* 1/2018 Huxham ............. G06F 21/6245

FOREIGN PATENT DOCUMENTS

EP        3210530 A1 \*  8/2017 ......... A61B 5/02438
WO     2013/075082      5/2013
(Continued)

OTHER PUBLICATIONS

International Search Report and Written Opinion dated Dec. 10, 2019 for International Application No. PCT/EP2019/077206 Filed Oct. 8, 2019.
(Continued)

*Primary Examiner* — David D Davis

(57) ABSTRACT

An apparatus, method, and computer program for identifying a user of a display unit. The apparatus comprises a processor configured to receive a physiological measurement for a first user; compare the received physiological measurement with a plurality of time series of physiological measurements, each time series corresponding to one of a plurality of users; and determine, based on the comparison, an identity of the first user.

19 Claims, 6 Drawing Sheets

(51) Int. Cl.
  *G02B 5/08*   (2006.01)
  *G06F 3/01*   (2006.01)
  *G06F 21/34*  (2013.01)

(56) References Cited

FOREIGN PATENT DOCUMENTS

| WO | 2017091440 | 6/2017 |
| WO | 2018004615 | 1/2018 |

OTHER PUBLICATIONS

Anonymous: "EatSmart Precision Tracker Digital Bathroom Scale", Jul. 1, 2018 https://eatsmartproducts.com/wp-content/uploads/sites/4/2018/06/ESBS-07_Instruction_Manual-EatSmart-Tracker-Scale.pdf.

Anonymous: "Taylor Smart Scale", Aug. 27, 2014.

Stephanie Bell: "The National Physical Laboratory is operated on behalf of the DTI by NPL Management Limited, a wholly owned subsidiary of Serco Group plc a Beginner's Guide to Uncertainty of Measurement Good Practice Guide", Mar. 31, 2001.

Jenkins, et al: "Using Ground Reaction Forces from Gait Analysis: Body Mass as a Weak Biometric", International Conference on Pervasive Computing, Pervasive 2007: Pervasive Computing pp. 251-267.

Srinivasan, et al: "Using Height Sensors for Biometric Identification in Multi-resident Homes", International Conference on Pervasive Computing, Pervasive 2010: Pervasive Computing pp. 337-354.

\* cited by examiner

APPARATUS, METHOD, AND COMPUTER PROGRAM FOR IDENTIFYING A USER OF A DISPLAY UNIT

CROSS REFERENCE TO RELATED APPLICATIONS

This application is the U.S. National Phase application under 35 U.S.C. § 371 of International Application No. PCT/EP2019/077206 filed Oct. 8, 2019, which claims the benefit of European Patent Application Number 18199615.8 filed Oct. 10, 2018. These applications are hereby incorporated by reference herein.

FIELD OF THE INVENTION

The invention relates to identifying users of devices and, in particular, to an apparatus for identifying a user of a display unit. The invention also relates to a method of identifying a user of a display unit.

BACKGROUND OF THE INVENTION

Many newly-manufactured electronic devices include functionality allowing them to communicate and interact with other devices. Many display units, such as televisions, include such functionality, allowing them to transmit signals to and receives signals from wirelessly-connected devices, such as smart phones, tablet computers and other computer devices.

One area in which display units are used is in the field of interactive mirrors, also referred to as smart mirrors. An interactive mirror is a unit which, in addition to functioning as a mirror to show a user his or her reflection, is also capable of displaying information to the user. Information, such as text, images and videos, may be displayed on a display portion of the interactive mirror which may, for example, be positioned behind a mirrored (or partially-mirrored) panel or a mirrored (or partially-mirrored) surface. In this way, the display screen of the interactive mirror, or portions thereof, may be visible through the mirror portion, so that a user is able to simultaneously view their reflection and information presented on the display screen.

Interactive mirrors may include functionality enabling them to interact with other devices, for example portable electronic devices. Interactive mirrors may be installed in a bathroom setting and, in such settings, the interactive mirror may be able to communicate with other devices in the bathroom setting, for example personal care devices, such as shaving devices, oral care devices, bathroom scales and the like.

One consideration to be taken into account when allowing devices to communicate and transmit data to one another is privacy and confidentiality. For example, a device (e.g. an interactive mirror) should be allowed to display personal, user-specific data only to the particular user to whom the data relates. Thus, it would be desirable for a display unit to be able to reliably identify a user so that personal data and information is not displayed to other users.

It is to be noted that the Taylor Smart Scale 7222F and the Eat Smart Precision Tracker Digital Bathroom Scale ESBS-07 claim to identify a user based on a single measurement out of a set of stored user profiles. The measured weight is compared to stored last measured weights in all stored profiles and user profiles are considered to correspond to the user standing at the scale when the difference is less than a predefined, fixed threshold.

SUMMARY OF THE INVENTION

Privacy is an important consideration when multiple users are able to access data from a single device. The privacy of users can be of even greater concern when the data relates to the health of the user, or is specific to the user in some other way. Thus, it is important that a display unit capable of interacting with other devices and, therefore, able to acquire personal data from various sources, is also able to restrict the presentation of such data to the relevant user, so that personal information is not shared with other people.

The inventors have recognized that the identity of a user may be determined using physiological data relating to the user. For example, physiological measurements may be acquired when a user uses one or more devices, such as personal care devices. By analyzing the physiological measurements of a user, it may be possible to determine the identity of the user and, therefore, determine which data (e.g. user specific data) is to be displayed to the user.

According to a first aspect, embodiments disclosed herein provide an apparatus for identifying a user of a display unit, the apparatus comprising a processor configured to receive a physiological measurement for a first user; compare the received physiological measurement with a plurality of time series of physiological measurements, each time series corresponding to one of a plurality of users; and determine, based on the comparison, an identity of the first user.

By using a time series of multiple physiological measurements, the processor is able to make a more accurate prediction of the physiological measurement that will be expected, and compare that expected measurement (or measurement range) with the received measurement to determine the user's identity. Thus, by using a time series of measurements rather than just a single measurement, the apparatus can determine the user's identity with a greater level of confidence, thereby reducing the chance likelihood that personal or confidential content relating to a user will be displayed to the wrong user. Furthermore, identifying the user in this way allows for a seamless (or nearly seamless) user experience, whereby the apparatus can take relevant action for the user (e.g. displaying user-specific content) based on the identification, without the user having to take addition action (e.g. manually entering login details).

In some embodiments, the processor may be configured to compare the received physiological measurement with a predicted range for each of the plurality of users, the predicted range being based on the time series of physiological measurements.

The predicted range for each of the plurality of users may be determined based on a goodness of fit model for each corresponding time series.

In some embodiments, comparing the received physiological measurement with a predicted range for a user of the plurality of users comprises determining whether the received physiological measurement falls within a range defined based on a corresponding time series.

Comparing the received physiological measurement with a predicted range for a user of the plurality of users may, in some embodiments, comprise determining whether the received physiological measurement falls within a range defined based on a most recent physiological measurement in the corresponding time series.

The defined range for each time series may vary with respect to time in the time series.

In some embodiments, the defined range for each time series may increase as a function of the time elapsed since the most recent physiological measurement in the time series was acquired.

The processor may, in some embodiments, be configured to deliver, based on the determination of the identity of the first user, data specific to the first user for presentation on the display unit.

In some embodiments, the processor may be configured to request a user input when the comparison reveals that the received physiological measurement is within a threshold range of physiological measurements of multiple users of the plurality of users; and determine, further based on the user input, the identity of the first user.

The received physiological measurement may, in some embodiments, comprise a first physiological measurement. The processor may be configured to receive a second physiological measurement for the first user; compare the received second physiological measurement with a plurality of time series of second physiological measurements, each time series corresponding to one of the plurality of users; and determine, further based on the comparison of the second physiological measurements, the identity of the first user.

In some embodiments, the physiological measurement may comprise at least one of a weight measurement, a height measurement, a blood pressure measurement, a heart rate measurement, a pulse measurement, a skin parameter measurement, a hair parameter measurement and a biometric measurement.

The physiological measurement may be received from a personal care device associated with the apparatus. In some embodiments, the apparatus may comprise an interactive mirror.

According to a second aspect, embodiments disclosed herein provide a computer implemented method for identifying a user of a display unit, the method comprising receiving a physiological measurement for a first user; comparing the received physiological measurement with a plurality of time series of physiological measurements, each time series corresponding to one of a plurality of users; and determining, based on the comparison, an identity of the first user.

According to a third aspect, embodiments disclosed herein provide a computer program product comprising a non-transitory computer-readable medium, the computer-readable medium having computer-readable code embodied therein, the computer-readable code being configured such that, on execution by a suitable computer or processor, the computer or processor is caused to perform steps of the methods disclosed herein.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Embodiments disclosed herein provide an apparatus for identifying a user of a display unit, so that user-specific content or data may be displayed or presented to the user. The identification of the user is performed by comparing an acquired physiological measurement of the user with a plurality of time series of physiological measurements corresponding to a plurality of users. If the acquired physiological measurement matches, or is similar to (e.g. within a defined range of) a most recent measurement in one of the time series of physiological measurements, then it may be determined that the user from whom the physiological measurement was acquired is the same as that the user corresponding to the matching (or similar) measurement. By taking into account a time series of physiological measurements, rather than a single measurement, a more reliable identity determination may be achieved, since changes in the physiological measurements over time can be taken into account.

As used herein, the expressions "time" and "time series" are intended to refer to a time based on a calendar and/or to an arbitrary machine unit of time. Thus, data points or measurements may be associated with or provided with a timestamp based on a human calendar date/time format (e.g. notated using the ISO8601 format), a machine time value (e.g. using POSIX time), and/or a specific machine processor 'tick' value that increments with time.

According to some embodiments disclosed herein, the display unit may comprise, or form at least part of, an interactive mirror, or smart mirror. For example, the display unit may form the display screen of an interactive mirror, such that a user is able to see their reflection in the reflective portion of the interactive mirror, and, at the same time, view content (e.g. information or data) presented on the display screen. However, it will be appreciated that the apparatus disclosed herein may identify a user of any type of display unit.

Figure 1:
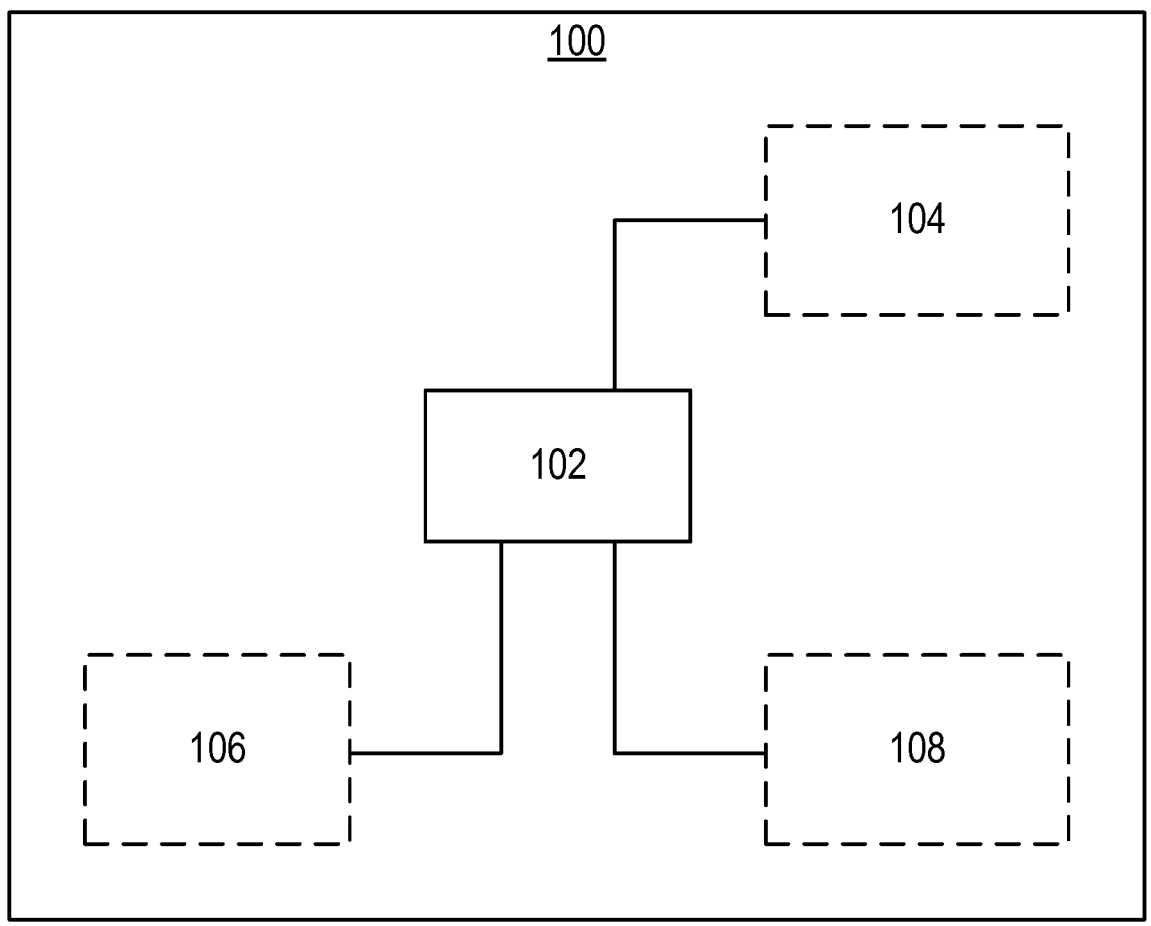
FIG. 1 is a schematic illustration of an example of an apparatus according to various embodiments.

According to a first aspect, embodiments disclosed herein provide an apparatus for displaying content on a display unit. Referring to the drawings, FIG. 1 shows a block diagram of an apparatus 100 that can be used for identifying a user of a display unit. The apparatus may, for example, form part of the display unit, or be in operative communication with the display unit. For example, the apparatus may comprise a computing unit or controller for operating a display unit. With reference to FIG. 1, the apparatus 100 comprises a processor 102 that controls the operation of the apparatus 100 and that can implement the methods described herein. The apparatus 100 may further comprise a memory 106 comprising instruction data representing a set of instructions. The memory 106 may be configured to store the instruction data in the form of program code that can be executed by the processor 102 to perform the methods described herein. In some implementations, the instruction data can comprise a plurality of software and/or hardware modules that are each configured to perform, or are for performing, individual or multiple steps of the method described herein. In some embodiments, the memory 106 may be part of a device that also comprises one or more other components of the apparatus 100 (for example, the processor 102 and/or one or more other components of the apparatus 100). In alternative embodiments, the memory 106 may be part of a separate device to the other components of the apparatus 100. For example, the apparatus 100 may be implemented as part of a cloud computing environment.

The processor 102 of the apparatus 100 can be configured to communicate with the memory 106 to execute the set of instructions. The set of instructions, when executed by the processor 102 may cause the processor to perform steps of the methods described herein. The processor 102 can comprise one or more processors, processing units, multi-core processors or modules that are configured or programmed to control the apparatus 100 in the manner described herein. In some implementations, for example, the processor 102 may comprise a plurality of processors, processing units, multi-core processors and/or modules configured for distributed processing. It will be appreciated by a person skilled in the art that such processors, processing units, multi-core processors and/or modules may be located in different locations and may each perform different steps and/or different parts of a single step of the methods described herein.

In some embodiments, as illustrated in FIG. 1, the apparatus 100 may comprise at least one user interface 104 configured to receive any of the user inputs described herein. The user interface may, for example, form part of, or cooperate with, the display unit (not shown in FIG. 1). The user interface 104 may allow a user of the apparatus 100 to manually enter instructions, data, or information relating to the method described herein. In some embodiments, the user interface 104 may be used to present content to a user. The user interface 104 may be any type of user interface that enables a user of the apparatus 100 to provide a user input, interact with and/or control the apparatus 100. For example, the user interface 104 may comprise one or more switches, one or more buttons, a keypad, a keyboard, a mouse, a touch screen, a microphone or an application (for example, on a tablet or smartphone), or any other user interface, or combination of user interfaces that enables the user to provide data to the apparatus and/or via which the user can consume information from the apparatus 100.

In some embodiments, the user interface 104 (or another user interface of the apparatus 100) may enable rendering (or output or display) of information, data or signals to a user of the apparatus 100. As such, a user interface 104 may be for use in providing a user of the apparatus 100 with information relating to or resulting from the method according to embodiments herein. The processor 102 may be configured to control one or more user interfaces 104 (e.g. the display unit) to provide information resulting from the method according to embodiments described herein. For example, the processor 102 may be configured to control one or more user interfaces 104 to render (or output or display) data using the methods described herein and/or any other outputs of the methods described herein. The user interface 104 may, in some embodiments, comprise a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces for providing information relating to, or resulting from the method, to the user. In some embodiments, the user interface 104 may be part of a device that also comprises one or more other components of the apparatus 100 (for example, the processor 102, the memory 106 and/or one or more other components of the apparatus 100). In alternative embodiments, the user interface 104 may be part of a separate device to the other components of the apparatus 100.

In some embodiments, as illustrated in FIG. 1, the apparatus 100 may also comprise a communications interface (or circuitry) 108 for enabling the apparatus 100 to communicate with any interfaces, memories and devices that are internal or external to the apparatus 100. The communications interface 108 may communicate with any interfaces, memories and devices wirelessly or via a wired connection. For example, the communications interface 108 may receive the signal indicative of the position of the user, and forward the signal to the processor 102.

It will be appreciated that FIG. 1 shows the components required to illustrate this aspect of the disclosure and, in a practical implementation, the apparatus 100 may comprise other components in addition to those shown. For example, the apparatus 100 may comprise a battery or other power supply for powering the apparatus 100 or means for connecting the apparatus 100 to a mains power supply.

Figure 2:
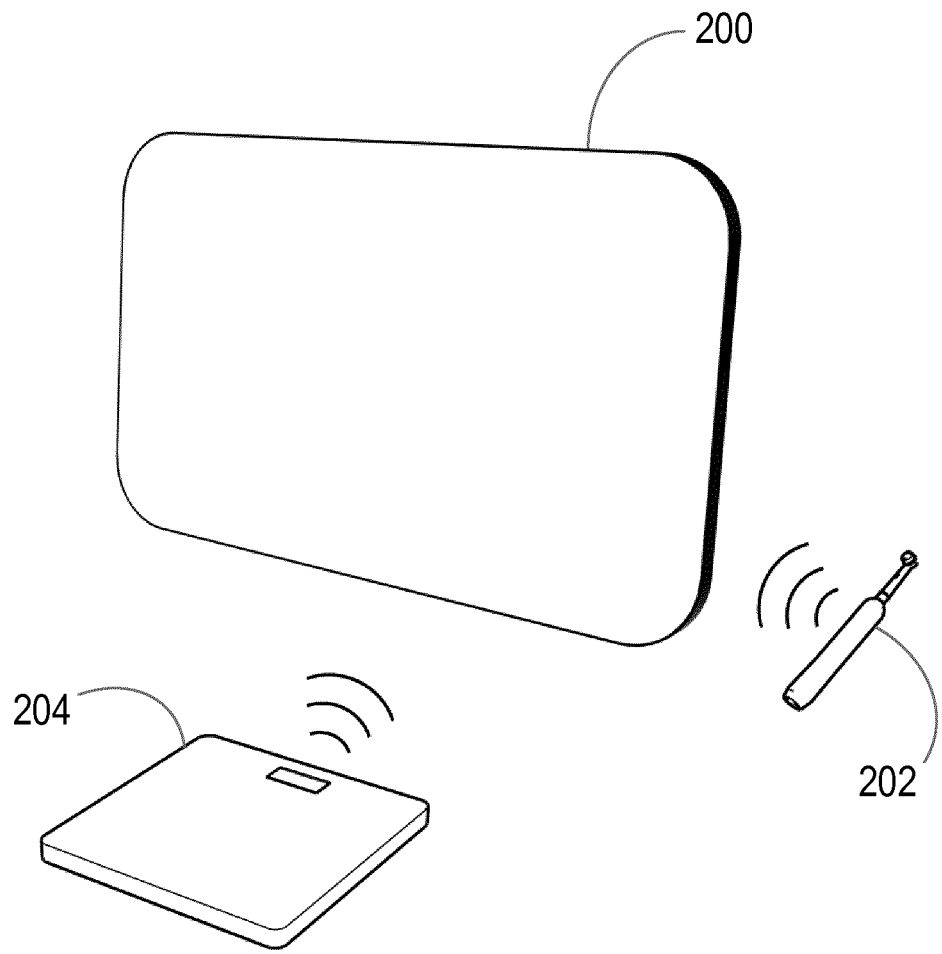
FIG. 2 is an illustration of an example of a display unit in communication with various devices.

FIG. 2 is an illustration of an example of a display unit 200 in communication with a first device 202 and a second device 204. In this example, the display unit 200 comprises an interactive mirror which may, for example, be installed in a bathroom setting, and the first and second devices 202, 204 comprise personal care devices. The first device 202 is, in this example, a connected toothbrush, and the second device 204 is, in this example, a scale (i.e. for measuring the weight of a user). In this example, a connected toothbrush is considered to comprise a toothbrush (e.g. a power toothbrush) capable of communicating with (e.g. transmitting data to and/or receiving data from) another device, such as the apparatus 100 and/or the display unit 200. It will be appreciated, however, that more or fewer devices may be in communication with the display unit 200, and the devices may comprise devices other than personal care devices, such as a smartphone. Similarly, the display unit 200 may comprise a device other than interactive mirror, which may be installed somewhere other than in a bathroom setting. In some examples, the device providing the physiological measurement to the apparatus 100 may comprise an intermediate device, which receives the measurement from a measurement-acquiring device (e.g. a connected toothbrush or a scale).

In the example shown in FIG. 2, the first device 202 and/or the second device 204 may be used by a user and, during their use, data relating to the user may be acquired. For example, the first device 202 (e.g. a connected toothbrush) may acquire data relating to brushing technique of a user and/or physiological data of the user. In some examples, the connected toothbrush may include means (e.g. a sensor) for acquiring biometric data of the user, such as a fingerprint sensor to acquire a fingerprint of the user. In other examples, another physiological measurement (e.g. a measurement relating to the user's teeth, gums, saliva or skin) may be acquired by the connected toothbrush. The second device 204 (e.g. a scale) may acquire a weight measurement of the user and/or other physiological data of the user, such as a measurement of the user's body fat. The first and second devices 202, 204 may be connected to the display unit 200 wirelessly (e.g. using Wi-Fi, Bluetooth, Infrared Data Association (IrDA) communication, or another known wireless communication), or via a wired connection. In general, it may be preferable for the physiological measurement of the user to be acquired simply as a result of the user using a particular device (e.g. the first device 202 or the second device 204). In this way, the user is not required to take any conscious action to be identified.

As noted above, the processor 102 is configured to perform steps of the methods described herein. In some embodiments, a memory (e.g. the memory 106) may be configured to store a set of instructions which, when executed by the processor 102 of the apparatus 100, cause the processor 102 to perform steps or functions as discussed below. The processor 102 is configured to receive a physiological measurement for a first user. The physiological measurement may be acquired by a device (e.g. the first device 202 or the second device 204) in real time, as the user is using the device. Alternatively, the physiological measurement of the user may be received or obtained from a memory (e.g. the memory 106) storing measurements acquired, for example by one or more devices.

The processor 102 is further configured to compare the received physiological measurement with a plurality of time series of physiological measurements, each time series corresponding to one of a plurality of users. The time series of physiological measurements for the plurality of users may, for example, be stored in a memory associated with and/or accessible by the processor 102 (e.g. the memory 106). The time series of physiological measurements for a user of the plurality of users may, for example, comprise a series of physiological measurements acquired in respect of that user on one or more occasions over a period of time. Each time series of physiological measurements may be associated with a user, and may be provided with a label identifying the user, such as the user's name or a reference or code specific to the user. When a new physiological measurement is received by the processor 102, the processor compares the measurement with the plurality of time series of physiological measurements associated with the plurality of users using one of a number of different methods as described below.

The processor 102 is further configured to determine, based on the comparison, an identity of the first user. In a general case, if the comparison reveals that the received physiological measurement for the first user matches, or is similar to (e.g. falls within a defined range of margin of) an average value or one of the time series of physiological measurements, or the most recent (i.e. latest) measurements in one of the time series of physiological measurements, then it may be determined that the corresponding to the matching, or similar, measurement can be identified as the first user.

For example, the apparatus 100 may form part of an interactive mirror installed in the bathroom of a family home. Interactive mirror may be used by a father, a mother, a son and a daughter. The interactive mirror may communicate with a scale used by the family members. Each time a family member uses the scale, their weight may be measured and stored in a memory device (e.g. the memory 106), in association with information identifying the family member, for example in a user profile. A user profile may be created for each new user of a device incorporating the apparatus 100 (e.g. the scale). When a family member steps onto the scale, a weight (i.e. a physiological measurement) measurement is acquired, and the processor 102 compares the weight measurement with the time series of weight measurements for the four family members. Based on the comparison, the processor 102 determines which family member is standing on the scale. In some examples, the determination of the identity may be used for displaying user-specific content on the interactive mirror, such as information relating to the user's weight, and how their weight has changed over time.

While, in some examples, a determination of the user's identity may be made straightforwardly from a comparison of the received physiological measurement with the plurality of time series of physiological measurements (e.g. if the time series of physiological measurements are all very distinct from one another), in other examples, such as when the time series of physiological measurements overlap with one another or are very close to one another, then it may be less straightforward to determine the identity of the user. Various techniques described herein may be used to enable the processor 102 to make a reliable identification of the user based on the time series of physiological measurements.

Figure 3:
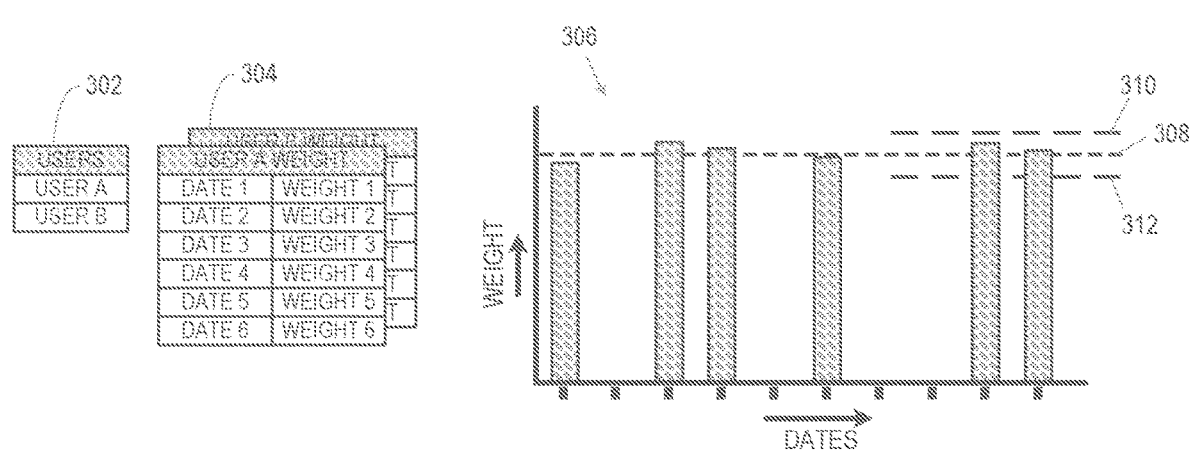
FIG. 3 is an illustration of an example of user data acquired by an apparatus.

Reference is now made to FIG. 3, which is an illustration of an example of user data acquired by the apparatus 100. Data may be acquired and stored (e.g. in the memory 106) for a set of users 302. In the example shown in FIG. 3, set of users 302 includes a first user (user A) and a second user (user B). For each user in the set of users 302, a time series 304 of physiological measurements may be acquired and stored. In this example, a plurality of weights are stored for each user, each weight having been acquired at a different time (on a different date). FIG. 3 also shows a chart 306 in which weights of a user (e.g. user A) are plotted as a function of time. The weights (or other physiological measurement) may fluctuate (e.g. increase and/or decrease) over time. The chart 306 includes a dashed line 308 representing an average (e.g. a mean) weight of the weight measurements plotted in the chart. Thus, a rudimentary prediction based on the recorded weights of the user a might be that a current weight of user A is around the average value. A slightly improved prediction may be achieved by taking into account the variation of weight measurements in the plotted weight measurements. For example, a standard deviation of the weight measurements may be calculated and used to determine a range or margin about the average value 308. In some examples, the standard deviation may be multiplied by some factor, determined from the measurements. The user's next weight measurement may be expected to lie within the range or margin. In FIG. 3, a predicted range is defined by an upper prediction threshold 310 and a lower prediction threshold 312. As will be clear to those skilled in the art, a set of measurements having a large variation (from the average value) will result in a larger range or margin than a set of measurements having a small variation. For example, if a user's weight were to remain substantially constant (e.g. within 0.5 kg over a large number of daily measurements), then the predicted range of values within which the next measurement will lie is likely to be very small. The range (e.g. the upper prediction threshold 310 and the lower prediction threshold 312) may be determined in some other way, which does not involve calculating a standard deviation. For example, the range may be determined using a set of rules or look-up tables. In other examples, the range may be determined based on a spread of the physiological measurements. The spread may be may be multiplied by some factor, determined from the measurements. By using a spread of the measurements rather than a standard deviation, the upper and lower limits of the range do not need to be symmetrical about the average value of the measurements.

In some examples, a device acquiring a physiological measurement may also record the time of the day at which the measurement was acquired. This may also be taken into account in determining the predicted range. Some physiological parameters, such as body weight and skin hydration may exhibit periodicity over the course of a day (i.e. over 24 hours).

In cases where not enough physiological measurements have been acquired to allow for a useful standard deviation to be calculated, a fixed expected variation may be determined. Such a fixed expected variation may, for example, be used as an initial starting range. In the example where weight measurements are acquired, upper and lower limits relative to the average weight may be determined, for example, using 0.5 kg+0.01×avg. weight. The initial range may then be adjusted by factoring the limits up or down, depending on how close subsequent measurements are to the evolving average measurement.

Thus, in some embodiments, the processor 102 may be configured to compare the received physiological measurement with a predicted range for each of the plurality of users, the predicted range being based on the time series of physiological measurements. In some embodiments, the predicted range for each of the plurality of users may be determined based on a goodness of fit model for each corresponding time series. Those skilled in the art will understand that various models may be used to determine a predicted value for a physiological measurement or a predicted range of physiological measurements based on previously-acquired physiological measurements (i.e. the time series) for a user. In some examples, an average value may be calculated as a rolling average, such that the average is updated with each new measurement added to the time series, or such that a new average is calculated based on the data in the latest defined time period (e.g. 28 days), or in the last defined number of data points. In some examples, the measurements the time series may be fitted to a curve using a function (e.g. a linear fitting function). The fitted curve may be extrapolated from the previously-acquired physiological measurements to a current time so as to determine a predicted value at the current time. In some cases, a linear fitting function will be sufficient to provide an accurate prediction. However, in other cases, a polynomial fitting function or an exponential fitting function may be used to generate a curve which having a more appropriate fit (e.g. result in a better goodness of fit) for the set of physiological measurements in the time series.

In a relatively straightforward case, comparing the received physiological measurement with a predicted range for a user of the plurality of users may comprise determining whether the received physiological measurement falls within a range defined based on a corresponding time series. Thus, for each user of the plurality of users, a range may be defined based on the corresponding time series of physiological measurements for that user, for example using the techniques discussed herein. If the comparison reveals that the received physiological measurement does fall within a predicted range for one particular user of the plurality of users, then it may be determined that the received physiological measurement has been acquired in respect of that particular user.

In some embodiments, the defined range may be based, at least in part, on a most recent physiological measurement in the time series of physiological measurements for a user. For example, a time series of physiological measurements for a user may show that the physiological measurement has remained substantially constant historically but, if the most recently-acquired physiological measurement in the time series shows a significant increase or a significant decrease, then this may affect the predicted range defined for that user. For example, in such a case, the predicted range may be substantially larger than it would have been if the latest physiological measurement had not varied so much from the previous average. Thus, in some embodiments, comparing the received physiological measurement with a predicted range for a user of the plurality of users may comprise determining whether the received physiological measurement falls within a range defined based on a most recent physiological measurement in the corresponding time series.

The predicted value or predicted range for the next physiological measurement in a time series for a user may depend on the time elapsed between subsequent physiological measurements. More specifically, the predicted range may depend at least in part on the time elapsed since the last (i.e. the most recent) physiological measurement in the time series of measurements was acquired. If, for example, the last weight measurement for a user was acquired less than one day ago, then it is unlikely that the weight of the user will have changed significantly from the most recently-acquired measurement. However, if the user's last weight measurement was acquired and recorded over a month ago, then there is a greater chance that their weight may have changed significantly since that last measurement. A model may be used to determine the predicted range which takes into account the time elapsed since the last measurement in the time series was acquired. Thus, the defined range for each time series may vary with respect to time in the time series.

Figure 4:
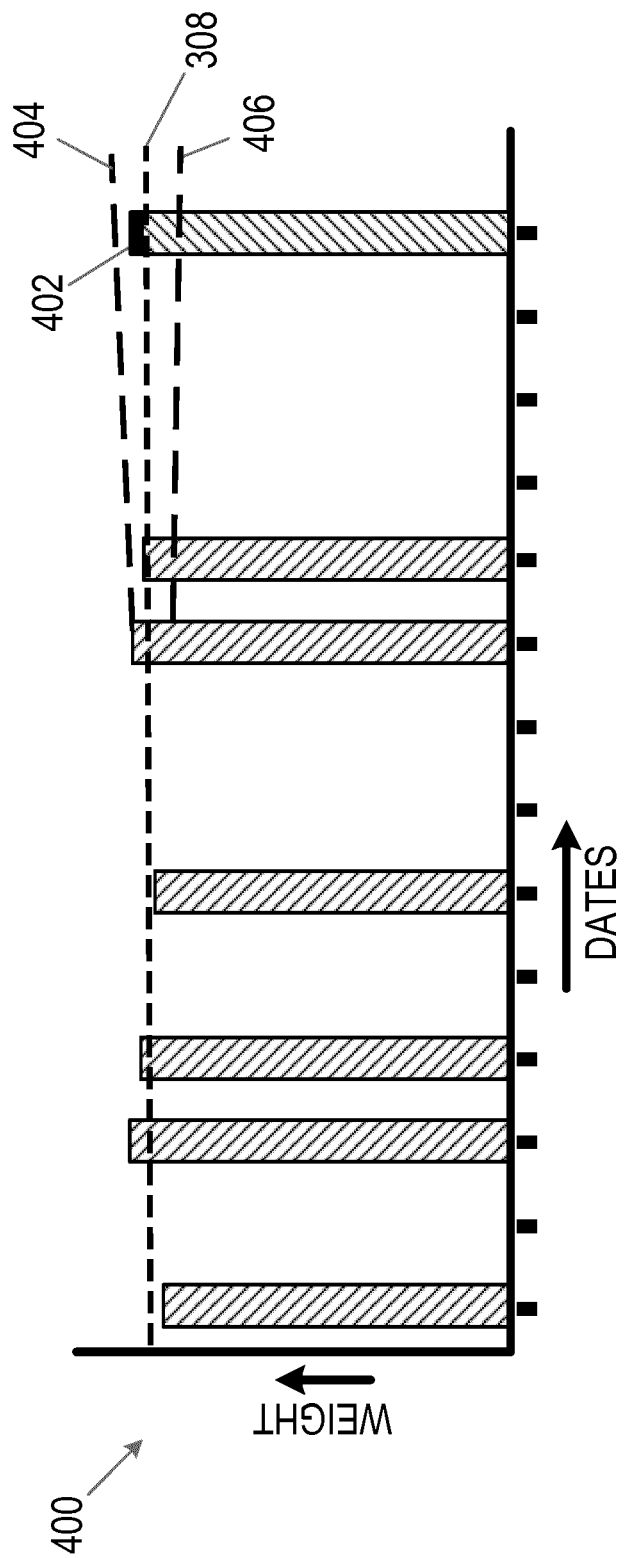
FIG. 4 is an illustration of a further example of user data acquired by an apparatus.

FIG. 4 is an illustration of a further example of user data acquired by an apparatus, such as the apparatus 100. FIG. 4 shows a chart 400 including the same physiological measurements shown in the chart 306 of FIG. 3. The chart 400 includes a dashed line representing the average 308 of the previously-acquired measurements. A current reading 402 is also shown. In this example, the predicted range, defined by an upper prediction threshold 404 and lower prediction threshold 406, is shown to vary over time. Specifically, the predicted range increases with time since the last acquired physiological measurement in the time series. In the example shown, the range increases linearly but, in other examples, the range may increase according to some other function (e.g. exponentially) with time. Thus, in some embodiments, the defined range for each time series may increase as a function of the time elapsed since the most recent physiological measurement in the time series was acquired. In the example of FIG. 4, the current reading 402 falls within the predicted range (taking into account the variation over time) and, therefore, it may be determined that the user in respect of whom the current weight reading has been acquired is the same user respect of whom the previous weight readings in the time series were acquired.

In some examples, if the elapsed time since the last recorded measurement in all of the time series (or in the most similar time series to the received measurement) exceeds a defined time limit (e.g. 30 days), then more prominence may be given to the first user's confirmation of their identity. In such cases, the processor 102 may not attempt to identify the first user, but may instead invite the first user to confirm their identity manually. The defined time limit may be defined by the processor 102 based on the measurements in the time series of measurements. For example, for a time series of measurements which vary greatly, the defined time limit may be relatively small, whereas for a time series of relatively constant measurements, the defined time limit may be relatively large.

If the received physiological measurement does not match a measurement or fall within a range of measurements of the time series of measurements, then it may be determined that the first user does not correspond to any of the users in the plurality of users. In some examples, the processor 102 may determine that the first user does not correspond to any of the users in the plurality of users if the difference between the received physiological measurement the average value or most recent value of the time series of physiological measurements exceeds a defined threshold value. Thus, the processor 102 may determine that the first user is a new user of the display unit. In such cases, the processor 102 may arrange for a "welcome new user" message to be displayed on the display unit 200, and may invite the first user to input personal details and/or to set up a new user profile. These details can be stored (e.g. in the memory 106) and used in future comparisons and user identifications.

In some examples, two or more users in respect of whom time series of measurements are recorded and accessed by the apparatus 100 may have similar predicted values (e.g. similar average values) and/or similar or overlapping predicted ranges. In such examples, it may not be possible to determine definitively whether a current reading is from one user or another. Therefore, in some embodiments, the predicted range may be defined based on a difference between physiological measurements (e.g. the most recent physiological measurement or an average of the physiological measurements) for users with the closest values to the received value.

For example, consider the scenario discussed above, in which two children of a family are users of a bathroom scale. One of the children may stand on the scale, and their weight measurement may be recorded and received by the processor 102. During the comparison of the received weight measurement against the time series of measurements of users, it may be determined that the received weight measurement is likely to belong to one of the two children. If the two children weigh approximately the same, then, the predicted ranges for the weights of the two children may overlap, such that the received weight falls within both predicted ranges. In this scenario, the processor 102 may be configured to adjust one or more of the predicted ranges so that the ranges no longer overlap. For example, the predicted range of the physiological measurements of the users (e.g. the ranges for the two children) may be adjusted (e.g. reduced) by the same amount such that the received weight measurement falls within just one of the predicted ranges.

In some examples, it may not be possible to reliably identify the user whose physiological measurement has been received (e.g. if the received measurement is particularly close to physiological measurements of two or more of the plurality of users). In such cases, the processor 102 may be able to determine that the first user (i.e. the user from whom the physiological measurement is received) is one of a subset users of the plurality of users. In other words, the processor 102 may be able to narrow down the selection of users, but it may not be able to determine the exact identity of the first user. In this way, the apparatus 100 may be seen to "almost" identify the first user, even though it is not possible to make a positive identification. Thus, the apparatus 100 may be said to provide "graceful degradation", whereby the identification of the first user is not seen to fail completely, but the apparatus has nearly succeeded in identifying the user. In other words, if two or more predicted ranges overlap, it is not possible to make a positive identification of the user, but it can be determined that the first user is one of the users having the overlapping ranges. Any user whose range overlaps the acquired measurement of the first user may be added to a list of candidates for identification. Further input may then be requested and/or obtained, in the form or an additional measurement (e.g. a second physiological measurement) or a user input/selection to enable the apparatus to determine the actual identity of the user from the candidates.

According to some embodiments, once the processor 102 has identified (or attempted to identify) the first user, and outcome of the identification (or attempted identification) may be presented to the user, for example on the display unit 200. For example, the processor 102 determines that the first user is the father of the family, then the processor may cause a message (e.g. a welcome message) to be displayed to the father. Once identification of the first user has been achieved, the processor 102 may provide the user with information specific to them, such as information including their user profile. In some embodiments, identifying the user may be used as part of a login process. Thus, the processor 102 may be configured to deliver, based on the determination of the identity of the first user, data specific to the first user for presentation on the display unit 200.

In cases where the processor 102 is not able to determine the identity of the user, but is able to determine a subset of the plurality of users, of which the first user is one, then the processor may present the subset on the display unit 200. For example, if the processor 102 is able to determine that the first user is one of the two children in the family, then the processor may present icons representing the two children on the display unit 200 (e.g. via the user interface 104), and invite the first user to select one of the icons, to thereby confirm their identity. In this way, the user would not need to search through a long list of possible users in order to identify themselves, but could quickly identify themselves from a shorter list, representing a subset of the plurality of users. Thus, the processor 102 may, in some embodiments, be configured to request a user input when the comparison reveals that the received physiological measurement is within a threshold range of physiological measurements of multiple users of the plurality of users. The processor 102 may be further configured to determine, further based on the user input, the identity of the first user.

If the processor 102 is not able to determine the exact identity of the first user then, in some embodiments, the processor may select a user in the plurality of users whose measurements are closest to the received measurement, and this selection may be presented to the first user (e.g. via the display unit 200) for confirmation. If the identification made by the processor 102 is incorrect in any embodiment, then a manual override may be available via the display unit 200/user interface 104 to enable a correct identity selection to be made by the first user.

In some examples, where the processor 102 is able to determine that the first user belongs to a subset of users of the plurality of users, one or more other items of data (e.g. one or more other physiological measurements) may be used to confirm the identity of first user. For example, if the apparatus 100 were able to communicate with a device which measures the height of a user while the user stands on a weighing scale, then the combination of the user's weight and height could be used to more accurately determine the identity of the user. Thus, the received physiological measurement may comprise a first physiological measurement (e.g. a weight measurement). The processor 102 may be further configured to receive a second physiological measurement (e.g. a height measurement) for the first user. The processor 102 may be configured to compare the received second physiological measurement with a plurality of time series of second physiological measurements, each time series corresponding to one of the plurality of users. The processor 102 may be configured to determine, further based on the comparison of the second physiological measurements, the identity of the first user. In some examples, it may not be necessary to compare the received second physiological measurement with an entire time series of second physiological measurements. For example, it may be sufficient to compare a second physiological measurement with a single stored physiological measurement for each user of the plurality of users, as some physiological attributes or parameters (e.g. height) may not vary significantly over time. Therefore, a user's height (or other physiological measurement) may be stored in association with their user profile, and used to confirm the identity of the user in the event that their identity cannot be confirmed using the first physiological measurement alone. The comparison of the received second physiological measurement with a plurality of time series of second physiological measurements may be performed using the techniques described above.

While the processor 102 may be considered to identify the first user reliably, the apparatus 100 may, in some embodiments, be provided with, or have access to, a secure authentication module or device, enabling a user to securely authenticate themselves, for example through a logging-on procedure.

In the above examples, various types of physiological measurement have been described. It will be apparent to the skilled person that measurements of a large range of physiological attributes may be acquired and used by the processor 102. For example, the physiological measurement may comprise at least one of a weight measurement, a height measurement, a blood pressure measurement, a heart rate measurement, a pulse measurement, a skin parameter measurement, a hair parameter measurement and a biometric measurement.

As noted previously, the physiological measurement may be received from a personal care device associated with the apparatus. For example, a weight measurement may be acquired using a weighing scale, a skin parameter measurement may be acquired using a skin care device, a hair parameter measurement may be acquired using a hair care device, and so on. This may be particularly beneficial when the apparatus 100 comprises, or is incorporated into or associated with, an interactive mirror, as such personal care devices are often used in conjunction with interactive mirrors.

Figure 5:
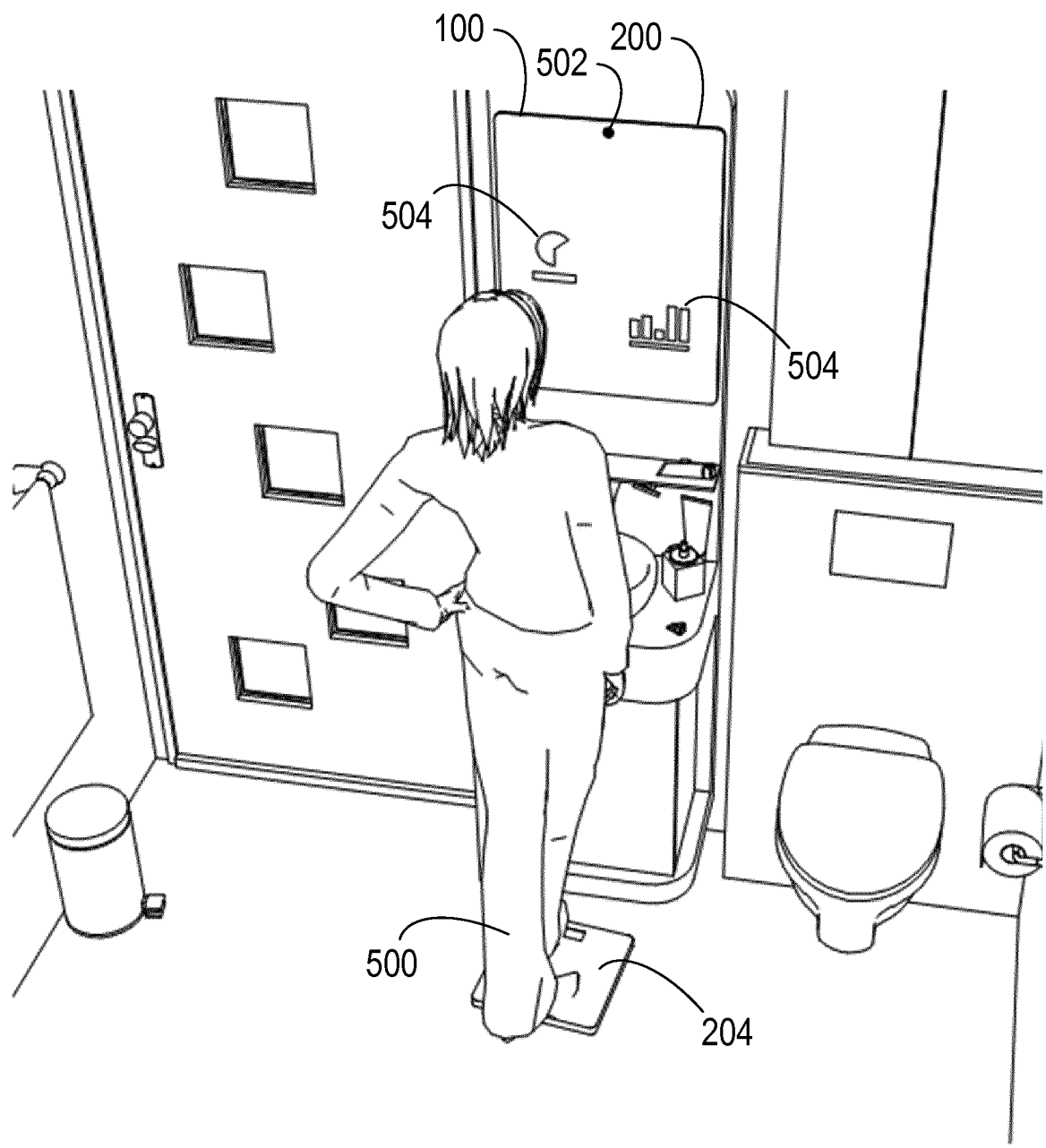
FIG. 5 is an illustration of an example of an apparatus in use in a bathroom setting.

FIG. 5 is an illustration of an example of the apparatus 100 in use in a bathroom setting. The apparatus 100 may form part of, or be in communication with the interactive mirror (e.g. the display unit 200), mounted in a bathroom environment. A user 500 may approach the mirror, for example to perform a personal care activity. In some examples, the mirror may be active as the user 500 approaches, or may "wake up" or become active upon detecting the approaching user, for example, via detection by a camera or image sensor 502 of the mirror. In a general mode, such as when the mirror becomes active, the mirror may display generic (e.g. non-user specific) content items 504, such as a weather forecast, or general news items, such that the user 500 can use the mirror for the personal care activity. The user 500 may start to use a personal care device, such as the second device 204 (e.g. a scale). In some examples, a physiological measurement of the user 500 may be acquired without the user taking any significant action. For example, the weight of the user 500 may be measured by the scale simply as a result of the user standing in front of the mirror (and on the scale). Once the physiological measurement of the user 500 has been acquired, the identification process discussed herein may begin automatically by the processor 102 of the apparatus 100. Once the user 500 has been identified, the mirror/display unit 200 may display user-specific content instead of or in addition to the content 504. Thus, the identification of the user 500 and the subsequent display of user-specific content may appear seamless and automatic to the user.

Figure 6:
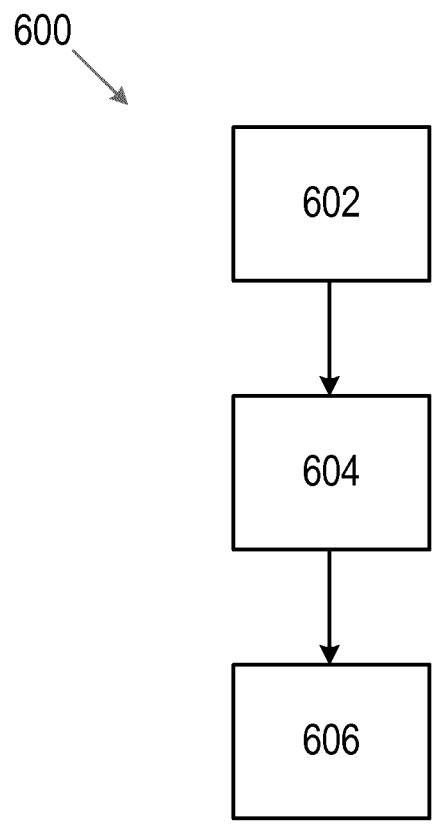
FIG. 6 is a flowchart of an example of a method according to various embodiments.

According to a second aspect, various embodiments disclosed herein provide a method. FIG. 6 is a flowchart of an example of a method 600 for identifying a user of a display unit, such as the display unit 200. The method 600 comprises, at step 602, receiving a physiological measurement for a first user. The received physiological measurement may comprise any type of physiological measurement, such as those discussed herein. At step 604, the method 600 comprises comparing the received physiological measurement with a plurality of time series of physiological measurements, each time series corresponding to one of a plurality of users. The method 600 comprises, at step 606, determining, based on the comparison, an identity of the first user. As will be apparent from the above discussion, steps of the method 600 may be performed using the apparatus 100 and/or the processor 102. According to embodiments, the method 600 may comprise one or more other steps corresponding to functions performed by the processor 102, as discussed herein.

Figure 7:
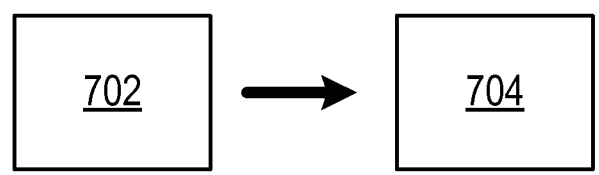
FIG. 7 is a schematic illustration of a processor in communication with a computer-readable medium.

According to a third aspect, various embodiments disclosed herein provide a computer program product. FIG. 7 is a schematic illustration of an example of a computer readable medium 704 in communication with the processor 702. According to some embodiments, a computer program product comprises a non-transitory computer-readable medium 704, the computer-readable medium having computer-readable code embodied therein, the computer-readable code being configured such that, on execution by a suitable computer or processor 702, the computer or processor is caused to perform steps of the methods disclosed herein.

The processor 102, 702 can comprise one or more processors, processing units, multi-core processors or modules that are configured or programmed to control the apparatus 100 in the manner described herein. In particular implementations, the processor 102, 702 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for identifying a plurality of users of a display unit, the apparatus comprising:
   a processor configured to:
      receive a physiological measurement for a first user of the plurality of users;
      obtain a plurality of time series of physiological measurements, each time series corresponding to one of the plurality of users;
      fit the plurality of time series of physiological measurements to a curve using a fitting function;
      determine, based on the fitted measurements, a predicted range of measurements for each of the plurality of users, wherein the fitted measurements are extrapolated from a previously acquired physiological measurement to a current time to determine a predicted value at the current time;
      compare the received physiological measurement with the predicted range of measurements for each of the plurality of users to distinguish an identity of the plurality of users, wherein the predicted range for each of the plurality of users is determined based on a goodness of fit model for each corresponding time series; and
      determine, based on the comparison, the identity of the first user.

2. The apparatus according to claim 1, wherein the predicted range of measurements is defined by an upper prediction threshold and a lower prediction threshold.

3. The apparatus according to claim 1, wherein comparing the received physiological measurement with the predicted range for the first user of the plurality of users comprises determining whether the received physiological measurement falls within a range defined based on a corresponding time series.

4. The apparatus according to claim 3, wherein the defined range for each time series varies with respect to time in the time series.

5. The apparatus according to claim 3, wherein the defined range for each time series increases as a function of the time elapsed since the most recent physiological measurement in the time series was acquired.

6. The apparatus according to claim 1, wherein comparing the received physiological measurement with a predicted range for a first user of the plurality of users comprises determining whether the received physiological measurement falls within a range defined based on a most recent physiological measurement in the corresponding time series.

7. The apparatus according to claim 1, wherein the processor is configured to:
   deliver, based on the determination of the identity of the first user, data specific to the first user for presentation on the display unit.

8. The apparatus according to claim 1, wherein the processor is configured to:
   request a user input when the comparison reveals that the received physiological measurement is within a threshold range of physiological measurements of multiple users of the plurality of users; and
   determine, further based on the user input, the identity of the first user.

9. The apparatus according to claim 1, wherein the received physiological measurement comprises a first physiological measurement, and wherein the processor is configured to:
   receive a second physiological measurement for the first user;
   compare the received second physiological measurement with a plurality of time series of second physiological measurements, each time series corresponding to one of the plurality of users; and
   determine, further based on the comparison of the second physiological measurements, the identity of the first user.

10. The apparatus according to claim 1, wherein the physiological measurement comprises at least one of a weight measurement, a height measurement, a blood pressure measurement, a heart rate measurement, a pulse measurement, a skin parameter measurement and a hair parameter measurement.

11. The apparatus according to claim 1, wherein the physiological measurement is received from a personal care device associated with the apparatus.

12. The apparatus according to claim 1, wherein the apparatus comprises an interactive mirror.

13. A computer implemented method for identifying a plurality of users of a display unit, the method comprising:
receiving a physiological measurement for a first user of the plurality of users;
obtaining a plurality of time series of physiological measurements, each time series corresponding to one of plurality of users;
fitting the plurality of time series of physiological measurements to a curve using a fitting function;
determining, based on the fitted measurements, a predicted range of measurements for each of the plurality of users, wherein the fitted measurements are extrapolated from a previously acquired physiological measurement to a current time to determine a predicted value at the current time;
comparing the received physiological measurement with the predicted range of measurements for each of the plurality of users to distinguish an identity of the plurality of users, wherein the predicted range for each of the plurality of users is determined based on a goodness of fit model for each corresponding time series; and
determining, based on the comparison, the identity of the first user.

14. A computer program product comprising a non-transitory computer-readable medium, the computer-readable medium having computer-readable code embodied therein, the computer-readable code being configured such that, on execution by a suitable computer or processor, the computer or processor is caused to perform the method of claim 13.

15. The method according to claim 13, wherein the predicted range is defined by an upper prediction threshold and a lower prediction threshold.

16. The method according to claim 13, wherein comparing the received physiological measurement with the predicted range for the first user of the plurality of users comprises determining whether the received physiological measurement falls within a range defined based on a corresponding time series.

17. The method according to claim 16, wherein the defined range for each time series varies with respect to time in the time series.

18. The method according to claim 16, wherein the defined range for each time series increases as a function of the time elapsed since the most recent physiological measurement in the time series was acquired.

19. The method according to claim 13, wherein comparing the received physiological measurement with a predicted range for the first user of the plurality of users comprises determining whether the received physiological measurement falls within a range defined based on a most recent physiological measurement in the corresponding time series.

* * * * *